United States Patent [19]

Yamamura et al.

[11] Patent Number: 4,544,632
[45] Date of Patent: Oct. 1, 1985

[54] HUMAN T CELL LINES AND METHOD OF PRODUCING SAME

[76] Inventors: Yuichi Yamamura, 9/22, Nigawatakadai 1-chome, Takarazuka-shi, Hyogo-ken; Tadamitsu Kishimoto, 5-31, Nakano 3-chome, Tondabayashi-shi, Osaka-fu, both of Japan

[21] Appl. No.: 384,427

[22] Filed: Jun. 2, 1982

[30] Foreign Application Priority Data

Jun. 12, 1981 [JP] Japan .................................. 56-91265
Aug. 4, 1981 [JP] Japan .................................. 56-122815

[51] Int. Cl.$^4$ ...................... C12P 21/00; C12N 15/00; C12N 5/00; C12R 1/91
[52] U.S. Cl. .................................. 435/68; 435/172.1; 435/172.2; 435/242; 435/948; 935/101; 935/109
[58] Field of Search .................. 435/68, 240, 172, 948

[56] References Cited

U.S. PATENT DOCUMENTS

| | | | |
|---|---|---|---|
| 4,401,756 | 8/1983 | Gillis .................................. | 435/240 |
| 4,407,945 | 10/1983 | Gillis .................................. | 435/172 |
| 4,434,230 | 2/1984 | Ritts, Jr. ............................ | 435/948 |
| 4,451,570 | 5/1984 | Royston ............................. | 435/948 |

FOREIGN PATENT DOCUMENTS 0044722 1/1982 European Pat. Off. ............ 435/948

OTHER PUBLICATIONS

Szybalski et al., "Genetics of Human Cell Lines I, 8-Azaguanine Resistance, A Selective Single-Step Marker", Proc. Soc. Exp. Biol. Med. 101, pp. 662-666 (1959).
Okada et al., "Establishment and Characterization of Human T Hybrid Cells Secreting Immunoregulatory Molecules", Proceedings of the National Academy of Sciences 78(12) (1981), pp. 7717-7721.
Irigoyen et al., "Generation of Functional Human T Cell Hybrids," Journal of Experimental Medicine 154 (1981), pp. 1827-1837.
Mier et al., "Purification and Some Characteristics of Human T-Cell Growth Factor from PHA-Stimulated Lymphocyte Conditioned Media", Proceedings of the National Academy of Sciences 77(10) (1980, pp. 6134-6138.
Maher et al., "Comparison of the Mutagenic Effect of UV Radiation and Chemicals in Normal and DNA-Repair Deficient Cells," Chemical Mutagens vol. 6 (1980), pp. 309-317.
Olsson et al., "Human Human Hybridomas Producing Monoclonal Antibodies of Predefined Antigenic Specificity," Proceedings of the National Academy of Sciences 77(9) (1980), pp. 5429-5431.
Harwell et al., "Concanavalin A-Inducible Interleukin-2-Producing T-Cell Hybridoma," Journal of Experimental Medicine 152 (1980), pp. 893-904.
Stull et al., "Constitutive Production of Interleukin 2 Activity by a T-Cell Hybridoma," Journal of Immunology 126(5) (1981), pp. 1680-1683.
Grillot-Courvalin et al., "Establishment of a Human T-Cell Hybrid Line with Suppressive Activity," Nature, vol. 292 (8-1981), pp. 844-845.

*Primary Examiner*—Thomas G. Wiseman
*Assistant Examiner*—John Tarcza
*Attorney, Agent, or Firm*—Larson and Taylor

[57] ABSTRACT

This invention provides a human parental T cell line which can fuse with normal human T cells, and hybrid cell lines which are prepared by fusion of the human parental T cells and the human T cells, and which are capable of producing lymphokines. This invention also provides methods of obtaining such human T cell lines, and a method of producing lymphokines from such hybrid cell lines.

12 Claims, 6 Drawing Figures

HUMAN T CELL LINES AND METHOD OF PRODUCING SAME

The present invention relates to novel human T cell lines, and more particularly to human T hybrid (fused) cell lines, especially human T hybrid cell lines that secrete lymphokines and a parental cell line that can fuse with human T cells to obtain such hybrid cells. This invention also relates to a method of establishing these cell lines, and to a method of obtaining the lymphokines from such cell lines.

Lymphocytes involved in the human immune system are generally classified into T cells, namely thymus-derived cells, and B cells, namely bone marrow-derived cells. It is known that B cells secrete antibodies. A technique has been established for obtaining monoclonal antibodies from B cell hybridomas prepared by cell hybridization of antibody-producing B cells and myeloma cells which serve as perental cells. (see "Rinsho Kagaku (Clinical Science)" Vol. 16, No.9, 1108-1114 (1980)).

T cells play a principal role in the regulation of immune response. While much still remains to be investigated as to their characteristics, it is known that T cells secrete many soluble immunoregulatory factors (lymphokines), such as a factor that suppresses antibody production, soluble factors that induce the proliferation of other T cells (interleukins), etc. However, these factors are secreted in very small amounts even in vivo, and furthermore, it is extremely difficult to produce, isolate or collect them in large quantities in vitro. Therefore, attempts have been made to prepare T hybrid cells by cell fusion in order to obtain such factors in vitro, but the several successful cases of T cell fusion so far reported are limited to only murine T cells. Nothing concerning the successful hybridization of human T cells has been reported yet. Human T parental cells which can be fused with human T cells have not been developed yet. Stated more specifically, even if such a parental cell for hybridization with the normal human T cell is obtained, the parental cell will revert to its original state before and/or during the hybridization process, thereby making the selection of hybridomas almost impossible. Furthermore, even if the hybridomas are selected and isolated, it is highly unpredictable that the hybridomas will be functionally stable or proliferate for a long time while retaining genes transferred thereinto from the normal T cell.

Since it is difficult to obtain large quantities of homogeneous soluble immunoregulatory factors, extreme difficulties are encountered in analyzing their chemical and biological characteristics. Thus no research has been done for the clinical application of these factors and their clinical effects. Furthermore, because human T hybrid cell lines have not been established yet, little or no progress has been made in the analysis of surface antigens on human T cells and T cell-receptors for antigens, in the investigation into the human T cell subset, and and in cellular and immunological studies on the differentiation, proliferation and activation of human T cells per se.

Accordingly an object of the present invention is to provide a parental cell line which can fuse with human T cells.

Another object of the invention is to provide a method of producing a parental cell line which can fuse with human T cells.

Another object of the invention is to provide novel hybrid cell lines produced from the parental cell line and human T cells.

Another object of the invention is to provide a method of producing the hybrid cell line.

Still another object of the invention is to provide a method of producing a large quantity of soluble immunoregulatory factors rapidly and easily in vitro by using the hybrid cell line.

These objects and other features of the invention will become apparent from the following description.

The present invention provides a hypoxanthine guanine phosphoribosyl transferase (HGPRT) deficient human T leukemic cell line, hybrid cell lines derived therefrom, and a method of establishing these cell lines. More specifically, the invention provides a novel parental T cell line which is not known in any way and makes possible fusion of human T cells, novel hybrid cell lines produced from the parental cell line and human T cells, and a method of producing such lines.

We have conducted extensive research to establish a human T cell fusion technique. Consequently, we have found that a specific cell line can fuse with human T cells, possesses sensitivity to the culture medium for selecting fused cells, is able to be maintained in culture permanently, and is suited as a parental cell line for preparing human T hybrid cells. We have also found that the line, when used as a parent, fuses with human T cells to give rise to human hybrid cells and that the hybrid cells can be easily selected with use of a selective medium. Furthermore, the clones obtained from the human T hybrid cells thus prepared include those which have the ability to produce soluble immunoregulatory factors (lymphokines) which are secreted from human T cells and are known to play an important role in regulating immune responses. The present invention has been accomplished based on these novel findings.

The parental cell line and the hybrid cell lines of the invention can be cultured continuously. With the establishment of these cell lines, especially the hybrid cell lines, it becomes possible to produce in vitro large amounts of soluble immunoregulatory factors which are secreted from human T cells, i.e. soluble factors which mediate intercellular reaction in immune response and to analyze the chemical and biological characteristics of these soluble factors which have not been fully clarified yet, contributing a great deal to the research on the clinical application and effect of these factors. Furthermore, the establishment of human T hybrid cell lines provides a very useful means for the analysis of surface antigens on human T cells and of T cell receptors for antigens, for the investigation into human T cell subset, and for cellular and immunological studies on the differentiation, proliferation and activation of human T cells per se.

The novel parental cell line of this invention is derived from a human T leukemic cell line and is characterized by being deficient in HGPRT. The cytological and other characteristics of the parental cell line are as follows.

(1) Morphological characteristics

The parental cells have about two to three times the diameter of normal human peripheral blood T cells and are nearly spherical. The nucleus occupies a large proportion of the cell, and a small amount of protoplasm is observed. The protoplasm includes some granules. A pseudopodium-like process may be found occasionally.

(2) Number of chromosomes

The parental cells are incubated in the presence of colchicine in a concentration of 0.1 μg/ml at 37° C. for 3 hours, centrifuged, treated with 0.075 M KCl and fixed on a slide glass with a mixture of methanol and ethanol (3:1). The number of nuclear chromosomes is thereafter counted microscopically by using a 1000× oil-immersion lens. The count for 100 cells in the meta phases ranges from 69 to 87 with an average of 78 and is listed in Table 1 below.

TABLE 1

| Number of chromosomes | 69 | 70 | 71 | 72 | 73 | 74 | 75 | 76 | 77 | |
|---|---|---|---|---|---|---|---|---|---|---|
| Number of cells | 1 | 3 | 4 | 4 | 4 | 4 | 4 | 11 | 12 | |
| Number of chromosomes | 78 | 79 | 80 | 81 | 82 | 83 | 84 | 85 | 86 | 87 |
| Number of cells | 10 | 9 | 4 | 9 | 5 | 10 | 2 | 1 | 2 | 1 |

(3) Expression of T cell specific antigen

The parental cells, $5 \times 10^5$ in number, are incubated with 100 μl of a monoclonal antibody in a suitable concentration (0.1 mg/0.5 ml of anti-Leu 1, anti-Leu 2A and anti-Leu 3A antibodies diluted 100-fold, 10-fold and 10-fold, respectively, to 100 μl) at 4° C. for 30 minutes. The monoclonal antibodies were provided by Becton-Dickinson Co., Sunnyvale, Ca, U.S.A. (J. Exp. Med., 153, 310–323 (1981)). The cells are thereafter washed with a MEM medium (obtained from the Research Institute for Microbial Diseases, Osaka University, Osaka, Japan) containing 5% FCS (fetal calf serum), reacted with FITC(fluorescein isothiocyanate)-conjugated rabbit anti-mouse immunogluobulin (Miles-Yeda Ltd., Israel), and then examined for the expression of T cell specific antigen by indirect immunofluorescence. When 200 of these cells are checked, at least 95% are positive for anti-Leu 1 and anti-Leu 3A antibodies, and up to 1% are positive for anti-Leu 2A antibody.

(4) Rosette formation

Two hundred parental cells are checked microscopically at 400× for Rosette formation with EAC (sheep red blood cells (E) treated with anti-erythrocyte antibody (A) and human complement (C)), with a result that up to 1% are positive.

(5) Expression of B cell marker

Surface immunoglobulin (Ig) is analyzed with use of FITC-conjugated mouse anti-human immunoglobulin (Behring Werke AG, Marburg) by direct immunofluorescence. Up to 1% of the cells are positive.

Human HLA-DR antigen (hereinafter referred to as "DR") is analyzed with use of a monoclonal anti-DR antibody (provided by Becton-Dickinson Co.) by indirect immunofluorescence. Up to 1% of the cells analyzed are positive.

Expression of human B cell specific antigen (B antigen) is analyzed by indirect immunofluorescence with use of a monoclonal anti-human B cell antibody obtained from a hybrid cell line prepared from myeloma $P3U_1$ (provided by Elbert Einstein College of Medicine) and mouse spleen cells immunized with a human B cell line (CESS, provided by Dr. Peter Ralph of Sloan-Kettering Institute for Cancer Research, New York, U.S.A.) transformed with a virus (Epstein-Barr virus) (see G. Kohler and C. Milstein, Nature, 256, 495, 1975). Up to 1% of the cells are positive. The antibody reacts with B cells or the lines thereof but does not react with T cells or the lines thereof.

(6) HLA phenotype

The parental cells are incubated with anti-HLA serum (provided by Prof. Sasazuki of Tokyo Medical and Dental University, Japan) at 37° C. for 30 minutes, thereafter incubated for 60 minutes with rabbit complement absorbed by the parental cell of this invention and then checked for survival. The HLA phenotype is A2, A11, B8, B37 and Bw 22.

(7) Proliferation

The parental cells proliferate satisfactorily in RPMI 1640 culture medium (Flow Laboratories, U.S.A.) containing 8-azaguanine (8-AG, 100 μM), 10% FCS, $5 \times 10^{-5}$ M 2-mercaptoethanol and 1 mM glutamine.

(8) Proliferation conditions

The parental cells generally proliferate satisfactorily at a temperature of 36° to 38° C. and pH of 7.2 to 7.3. It is suitable to use an incubator containing 5% carbon dioxide and 95% air.

(9) Continuous culture

The parental cells can be incubated continuously and indefinitely.

(10) Preservation in frozen form

The parental cells can be preserved in liquid nitrogen for a prolonged period of time.

(11) Resistance to 8-azaguanine

The parental cells are resistant to 8-azaguanine (100 μM) and dies in a medium (HAT medium) containing hypoxanthine, aminopterin and thymidine. This indicates that the parental cells are deficient in HGPRT.

(12) Mitogen responsiveness

When 10 to 100 μg/ml of concanavalin A (Con A) and 1 to 10% of plant lectin, phytohemagglutinin (PHA) are added to the medium, the proliferation of the parental cell line is inhibited to some extent. Pokeweed mitogen (PWM), as well as protein A (Pro A), produces no influence on the proliferation of the line at any concentration whatever.

Figure 1:
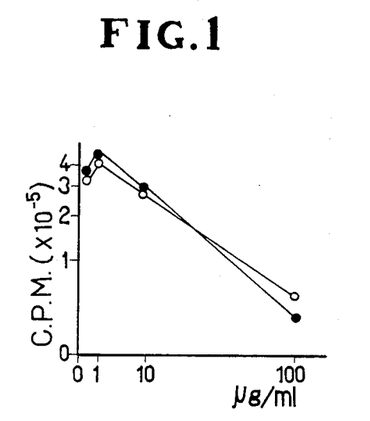
FIGS. 1 through 4 show graphs illustrating the mitogen responsiveness of the parental cell line CEM-AGR ® and the T cell line (clone No. 24-A) according to the present invention.
Figure 2:
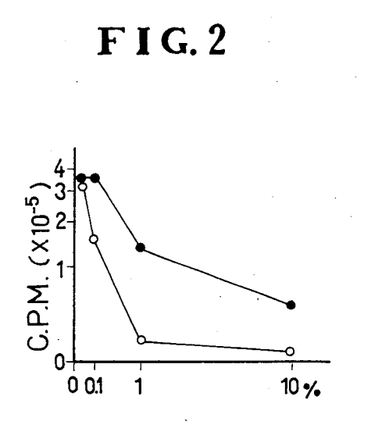
Figure 3:
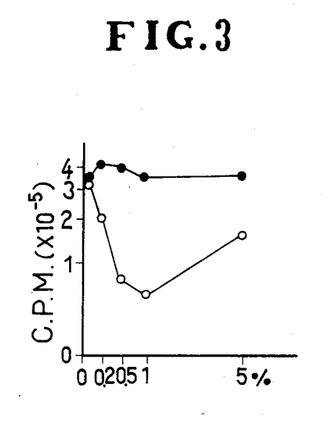
Figure 4:
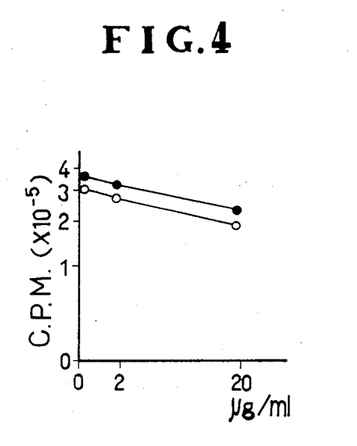

FIGS. 1 through to 4 show these characteristics. $2 \times 10^4$ cells of the present parental cell line are cultured in the presence of various concentrations of mitogens (FIG. 1 for Con A, FIG. 2 for PHA, FIG. 3 for PWM and FIG. 4 for Pro A) for 60 hours in RPMI 1640 medium containing 10% FCS. 0.2 μCi of $^3$H-thymidine ($^3$H-TdR) is added to the medium during the last 12 hours of culture. The cultures are harvested on glass fiber strips (Labo-Science Cell Harvester, Tokyo), and $^3$H-TdR uptake in deoxyribonucleic acid fraction is determined by liquid scintillation counting. In each experiment, cultures are set up in triplicate, and the mean values (up to 10% in S.D.) are presented. In each graph, the concentration of the mitogen is plotted as the abscissa, and the $^3$H-TdR count (C.P.M. $\times 10^{-5}$) as the ordinate. The one line (●——●) represents the result achieved with the present parental cell line, and the other line (○——○) represents the result with clone 24A (a clone of the human T hybrid cell line of the invention) to be described later.

The HGPRT-deficient human T leukemic cell line of the invention having the foregoing characteristics is derived, for example, from human T leukemic cells (CCRF-CEM) (J. KAPLAN, T. C. SHOPE and W. D.

transferred to a usual medium. For illustrative purposes, the characteristics of fused cells obtained in Examples to follow are given in Table 2 below in comparison with those of the parental cell line (i.e. HGPRT-deficient human T leukemic cells, hereinafter referred to as "CEM-AGR ®").

Approximately similar to the parental cells in every clone.

(11) Resistance to 8-azaguanine
No clone is resistant to 8-azaguanine.

(12) Mitogen responsiveness
The hybrid cell lines are comparable to or higher

TABLE 2

| Hybrid cell No. | Human T cell | Frequency | Clone No. | Chromosome number (average) | Expression of T cell specific antigen | | | Rosette formation | | Expression of B marker | | |
|---|---|---|---|---|---|---|---|---|---|---|---|---|
| | | | | | Leu 1 | Leu 2A | Leu 3A | E | EAC | Ig | DR | B antigen |
| 1 | Unstimulated PBL-T | 1/12 | 24-A | 79–97 (89) | ++ | − | ++ | − | − | − | − | − |
| 2 | Con A-stimulated Tonsil-T | 1/24 | 36-B | 79–100 (89) | ++ | − | ++ | − | − | − | − | − |
| 3 | Con A-stimulated PBL-T | 1/8 | 38-B | 79–96 (88) | ++ | − | ++ | − | − | − | − | − |
| 4 | PPD-stimulated PE-T | 1/8 | 41-III | 75–93 (86) | ++ | − | ++ | − | − | − | − | − |
| 5 | Unstimulated PBL-T | 1/24 | 43-A | 88–99 (93) | ++ | − | ++ | − | − | − | − | − |
| 6 | Pro A-stimulated PBL-T | 1/24 | 47-A | 81–98 (89) | ++ | − | ++ | − | − | − | − | − |
| 7 | Pro A-stimulated PBL-T | 4/12 | 40-VI | 82–91 (87) | ND | − | ND | − | ND | ND | ND | ND |
| 8 | Pro A-stimulated PBL-T | 5/24 | 44-C | 89–100 (94) | ND | − | ND | − | ND | ND | ND | ND |
| 9 | Pro A-stimulated PBL-T | 3/24 | 47-B | 87–100 (93) | ND | − | ND | − | ND | ND | ND | ND |
| Parental cell | CEM-AG$^R$ | − | − | 69–87 (78) | ++ | − | ++ | − | − | − | − | − |

The frequency listed in Table 2 is given by A/B where A is the number of wells containing established hybrid cells, and B is the number of wells seeded with $2 \times 10^5$ fused cells immediately after fusion.

The number of chromosomes, expression of T cell specific antigen, rosette formation and expression of B cell marker are determined by the same methods as already stated for the parental cell line. The symbols in the above table represent the following.

++ ... At least 95% of cells are positive.
− ... Up to 1% of cells are positive.
ND ... Not done.
E ... Sheep red blood cells.

Summarized below with reference to Table 2 are various characteristics of the human T hybrid cell line which include the same items (1) to (12) given for the parental cells and item (13).

(1) Morphological characteristics

The characteristics of the line, although slightly different from clone to clone, are substantially similar to those of the parental cell line. The line is slightly larger than the parental line (1.2 to 1.5 times as large). Many of the cells have numerous whisker-like projections on the surface.

(2) Karyotype (number of nuclear chromosomes)

Although the chromosome number varies from clone to clone, the mean chromosome number is in the range of 86 to 94 and is apparently larger than that of the parental cells which is 78.

(3) to (5)

Identical with the parental cells in a majority of clones.

(6) HLA phenotype

The phenotypes of the parental cells are observed in every clone. At least one HLA phenotype of the human T cells, other than those of the parental cells, is observed in every clone.

(7) to (10)

than the parental cell line in responsiveness to Con A and PHA. While the parental cell line has no responsiveness to PWM, a number of clones are found responsive to PWM.

(13) Producibility of lymphokines

Certain hybrid clones are capable of producing lymphokines, especially helper factors. For example, clones No. 24-A, No. 38-B, etc. have ability to produce T cell growth factor (TCGF) by the method to be described in Examples to follow. Furthermore, the clones are functionally stable, i.e. capable of producing TCGF by continuous culture for a long time.

The characteristics stated above indicate that novel human T hybrid cell lines are established by the present invention. The establishment of the hybrid cell lines is substantiated by the fact that the clones obtained are not resistant to 8-AG unlike the parental cell line, have an increased number of nuclear chromosomes and exhibit HLA phenotypes other than those of the parental cell line.

The human T hybrid cell lines of the invention thus obtained, when proliferated in a usual medium by a usual method, can be cloned, whereby the lines can be separated into individual monoclonal hybrid cell lines each of which has at least one nuclear chromosome of the human T cell. The line can be proliferated by continuous culture while retaining characteristics based on the genes transferred from the human T cell and is preservable when frozen, making it possible to investigate into human T cells in greater detail. The clones include those capable of producing various lymphokines, especially helper factors such as TCGF which are secreted from human T cells and which are known to play an important role in regulating immune response, so that through the establishment of such clones, it is possible to produce large quantities of lymphokines in vitro easily and rapidly and thereby provide PETERSON, Jr., J. Exp. Med. 139, 1070–1076, 1974) and can be obtained by culturing such cells in RPMI 1640 medium containing 10% FCS and 8-azaguanine (8-AG) and then successively transferring these cells to such media with increased concentrations of 8-AG. Stated more specifically, the cells are cultured in this type of medium containing, for example, 2 μM of 8-AG for 1 week first, then in the same medium containing 16 μM of 8-AG for 1 week and thereafter similarly in media with the concentration of 8-AG increased 2-fold in succession. Finally an 8-AG resistant cell line is obtained alive in a medium containing 100 μM of 8-AG. The resulting cell line briskly proliferates in the medium with 100 μM of 8-AG and can be cultured continuously in the same medium.

The line thus obtained has the foregoing characteristics, is a novel T cell line which has not been reported before, can be cultured permanently, and can be preserved by freezing almost indefinitely.

The HGPRT-deficient cell line of this invention can be cultured in various nutrient media which are substantially synthetic but which may contain a natural ingredient, such as serum. Examples of useful nutrient media are RPMI 1640 medium (Flow Laboratories, U.S.A.) modified with FCS, horse serum or a serum-like supplement, and Dulbecco medium modified with Iscove modified medium free from serum. The cells of this invention to be grown on such media can be readily adapted to proliferate on various media which are generally used in the art, such as FCS-containing minimum essential Eagle media (MEM). To maintain the parental cells of this invention, such media need not always contain 8-AG but preferably contain 8-AG. The cell can be cultured in these media under the conditions which are generally employed for the cultivation of usual cells. Generally, the parental cells can be proliferated satisfactorily at about 36° to about 38° C., with the liquid component replaced every 3 to 5 days.

Although the foregoing parental cell line was not accepted for deposition in the Fermentation Research Institute, Agency of Industrial Science and Technology, Japan, it is preserved by us always in a condition available to the public. Furthermore, a sample of the cell line was deposited at the American Type Culture Collection (ATCC), 12301 Parklawn Drive, Rockville, Md. 20852, U.S. on July 30, 1981, and has been assigned the ATCC number CRL 8081.

The HGPRT-deficient T cell line of the invention can be used as a parental cell line for fusing human T cells. The invention also provides a method of fusing T cells with the parental cell line and the T hybrid cell line thereby obtained.

The human T cells which can be used for T cell fusion are not particularly limited. Examples of useful T cells are those obtained from the peripheral blood, bone marrow, lymphonodes, spleen, tonsils, thymus, etc. Such T cells can be isolated and purified by various separating methods which are known, such as conventional physical methods, chemical methods and the adherence method to surface membranes, and can be used for cell fusion according to the invention. To achieve an improved fusion efficiency, these T cells can be stimulated with various mitogens before fusion. Examples of useful mitogens are those having sensitivity to T cells, such as concanavalin A (Con A, Sigma Chemical Co., St. Louis, Mo., U.S.A.), purified tuberculin (PPD, provided by Dr. Takatsu, Institute for Cancer Research, Osaka University Medical School, Osaka, Japan), protein A (Pro A, Pharmacia Co., Sweden), phytohemagglutinin (PHA, Difco, Detroit, Mich., U.S.A.), pokeweed mitogen (PWM, GIBCO Laboratories, U.S.A.), etc. The T cells to be used can also be activated by mixed lymphocyte culture. Examples are given later in which the production of human T cells and mitogen-stimulated T cells is described in detail.

The fusion reaction between the HGPRT-deficient human T leukemic cells and human T cells is conducted substantially in the same manner as in the known method of cell fusion in the presence of a fusion promotor in a suitable medium. Viruses, such as the Sendai virus (HVJ), are usable as fusion promotors, but it is preferable to use recently developed polyethylene glycol (PEG) as the promotor. It is preferable to use PEG having an average molecular weight of about 1000 to about 6000. It is suitable that the medium contain such PEG at a concentration of about 30 to about 60 W/V %. Useful culture media are MEM medium as it is or as modified with Dulbecco medium, RPMI 1640 medium and other media which are usually used for culturing cells. When desired, the medium may have incorporated therein dimethyl sulfoxide or like auxiliary agent for improving the fusion efficiency.

The proportions of parental cells of this invention and human T cells to be used for fusion are not particularly limited. Generally, the number of human T cells can be about 1 to about 10 times the number of parental cells. Preferably the cells are fused, for example, in the following manner. Specified quantities of parental cells and human T cells are thoroughly mixed together in the medium, the mixture is centrifuged, and the resulting supernatant is discarded. A suitable amount of a PEG solution heated to 37° C. is then admixed with the remaining mass, whereby cell fusion reaction is initiated. With the addition of a suitable medium, the mixture is centrifuged, and the supernatant is discarded. This procedure is repeated, and the desired fused cells are produced.

The desired fused cells can be selectively obtained by culturing the resulting mixture with a usual selective medium which permits proliferation of the desired hybrid cells only, but inhibits proliferation of the parental cells. (Inherently the human T cells are incapable of proliferating in the selective medium.) Typical of such media is, for example, a medium containing hypoxanthine, aminopterin and thymidine (HAT medium). More specifically, a useful example of HAT medium is prepared by adding $4 \times 10^{-7}$ M aminopterin, $1 \times 10^{-4}$ M hypoxanthine, $1.6 \times 10^{-5}$ M thymidine and, if desired, $3 \times 10^{-6}$ M glycine to a MEM or RPMI-1640 medium containing 10 to 20% FCS. The cells are cultured in the HAT medium by the usual limiting-dilution method for a period of time, usually several days to several weeks, sufficient to allow death of cells (e.g. unfused cells, etc.) other than the desired hybrid cells, whereby only the desired human T fused cells are selectively proliferated.

The fused cells thus obtained have novel characteristics distinct from those of the parental cell line and human T cells, in respect to their karyotype (number of nuclear chromosomes), phenotype of cell surface, mitogen responsiveness, lymphokine producibility, etc. Although the fused cells can be further proliferated continuously in a suitable medium such as the one already mentioned, it is preferable that the selectively prepared cells be cultured in HT medium containing hypoxanthine and thymidine for 1 to 2 weeks and thereafter novel means for the diagnosis and treatment of diseases of the immune system.

A detailed description will be given of one of the human T hybrid cell lines established and isolated by the present invention, namely clone No. 24-A. As will become apparent from Examples to follow, this clone is one of the hybridomas obtained by the fusion of the parental cell line and human T cells obtained from peripheral blood lymphocytes and has various properties which are common with the above-mentioned hybrid cell lines. In particular, the nuclear chromosome number of the clone is 79 to 97 (89 on the average). The clone exhibits HLA phenotypes of A2, AW24, A11, B5, B8, B37 and BW22 including those of the parental cell line (A2, A11, B8, B37 and BW22) and also those of the human T cell (A2, AW24, B5 and B40) except B40. The cloned cell line exhibits the responsiveness to mitogens shown in FIGS. 1 to 4. Thus the proliferation thereof is almost completely inhibited at 1% PHA and is also inhibited at a PWM concentration of 0.5 to 1%.

Figure 5:
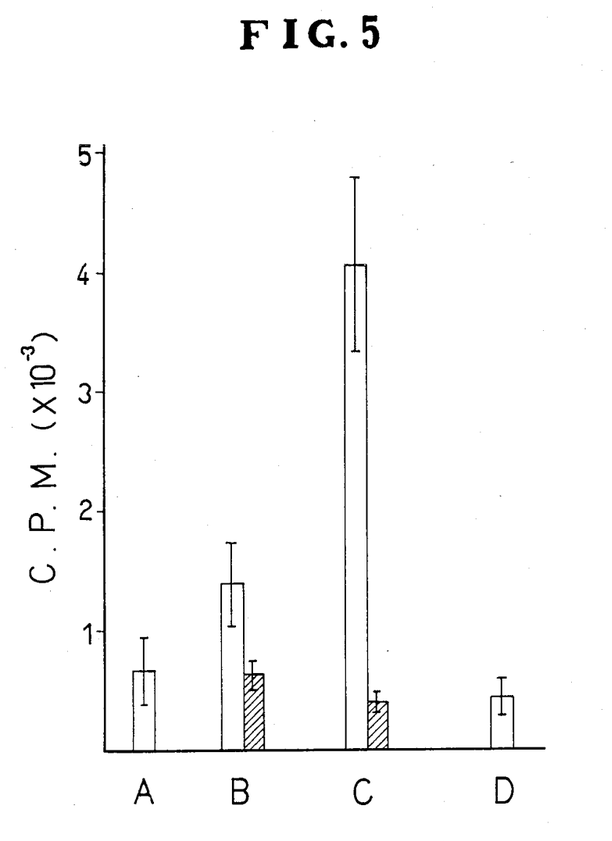
FIGS. 5 and 6 show graphs illustrating the TCGF activities of the T hybrid cell line (clone No. 24-A) according to the present invention.
Figure 6:
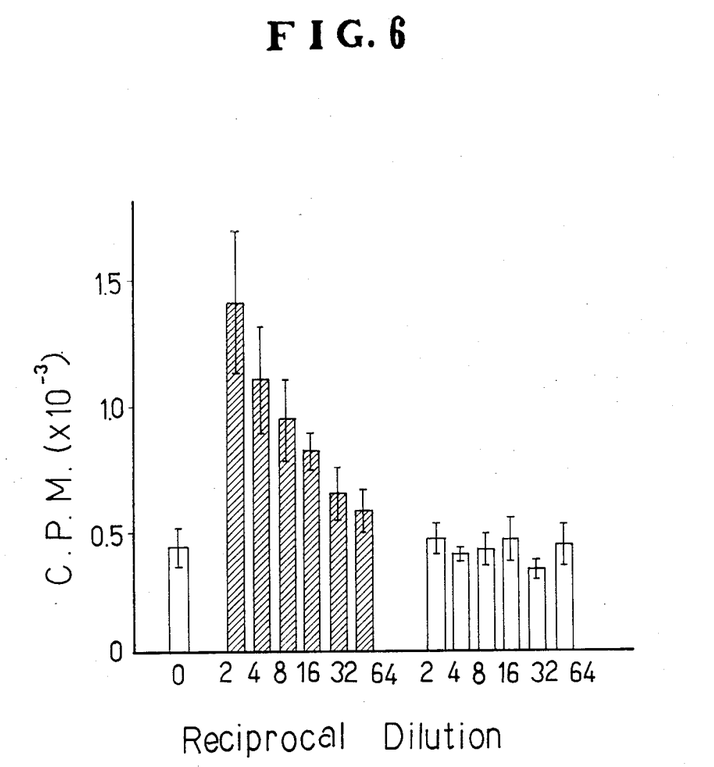

The clone is further characterized by high TCGF activity as will be apparent from Examples and FIGS. 5 and 6.

When the clone of the invention described above is cultured with the suitable medium mentioned above, the human T cell growth factor (TCGF) can be collected from the resulting supernatant. Accordingly the present invention also provides a novel method of producing the TCGF. The method will be described in detail in one of Examples to follow.

Since the novel fused cell line having the ability to produce TCGF was not accepted for deposition in the Fermentation Research Institute, Agency of Industrial Science and Technology, Japan, a sample of the line is maintained by us in a condition available to the public. A sample was deposited on July 30, 1981 at ATCC, 12301 Parklawn Drive, Rockville, Md., 20852, U.S.A., and has been assigned the ATCC number HB8082.

The present invention will be described in greater detail with reference to the following examples of preparation of the parental cell line, isolation of human T cells, fusion of such cells and testing of the fused lines obtained.

EXAMPLE 1

Preparation of HGPRT deficient human T leukemic cells

Human T leukemic cell line CCRF-CEM provided by Dr. Minowada, RPMI, Buffalo is cultured in RPMI 1640 medium (Flow Laboratories) containing 10% FCS (Centaurus, Biological Co., Lot No. 527).

The CCRF-CEM cells are suspended in RPMI 1640 medium containing 2 $\mu$M of 8-AG and modified with 10% FCS in a conentration of $1 \times 10^6$ cells/ml. A 10-ml portion of the suspension is placed into a culture bottle (Corning Glass Works, Corning, N.Y. U.S.A.) and maintained for incubation in an incubator at 37° C. for 1 week, with the bottle placed horizontally while passing a mixture of 5% carbon dioxide and 95% air therethrough. The surviving cells are collected, suspended in a concentration of $1 \times 10^6$ cells/ml in the same type of medium containing 8-AG at twice the above concentration, i.e. 4 $\mu$M, and similarly cultured for 1 week. The cells surviving the preceding culture procedure are cultured every week with use of a fresh medium, with the concentration of 8-AG increased about 2-fold every week (i.e. 2→4→8→16→32→50→75→100 $\mu$M) to finally obtain surviving cells in the medium containing 100 $\mu$M of 8-AG. Thus the desired 8-AG resistant cell line is obtained in about 8 weeks. The line is referred to as "CEM-AGR ®". The line thereafter grows briskly on RPMI 1640 medium containing 8-AG in the same concentration (100 $\mu$M) and modified with 10% FCS and has since been maintained in the same medium by the continuous culture. The line has the same cytological and other characteristics as already described.

EXAMPLE 2

Preparation and isolation of human T cells (1) Peripheral blood T cells

A 50 ml quantity of heparinized-blood collected from a healthy human adult is centrifuged with use of a lymphocyte separation liquid in density gradient ("Ficoll-Paque", a product of Pharmacia Japan Co., Ltd., Japan) to isolate $5 \times 10^7$ peripheral blood lymphocytes. T cells are isolated from the lymphocytes by rosetting with neuraminidase-treated sheep erythrocytes (SRBC) (T. HIRANO, T. KURITANI, T. KISHIMOTO and T. YAMAMURA, J. Immunol., 119, 1235–1241 (1977)). The peripheral blood T cells thus prepared are referred to as "unstimulated PBL-T".

The unstimulated PBL-T ($1 \times 10^6$ cells/ml) are stimulated with 10 $\mu$g/ml of Con A, 25 $\mu$g/ml of PPD or 10 $\mu$g/ml of Pro A for 48 hours to obtain stimulated T cells, which are referred to as "Con A-stimulated PBL-T", "PPD-stimulated PBL-T" or "Pro A-stimulated PBL-T", respectively.

(2) T cells from tonsilla palatina

The tonsil removed from the tonsilla palatina of a patient with chronic tonsillitis is cut into small fragments with use of MEM medium containing 10 units/ml of heparin and 4 $\mu$g/ml of Amphotericin-B (Sankyo Co., Ltd., Japan) to obtain tonsillar cells. The cells are centrifuged by the Ficoll-Paque density gradient method to isolate $5 \times 10^8$ tonsillar lymphocytes. Tonsillar T cells ($2 \times 10^8$) are isolated therefrom in the same manner as in (1) above by rosetting with neuraminidase-treated sheep erythrocytes. The cells ($1 \times 10^6$ cells/ml MEM) are stimulated with 10 $\mu$g/ml of Con A for 48 hours to obtain stimulated tonsillar T cells, which are referred to as "Con A-stimulated Tonsil-T".

(3) T cells from pleural effusion

Lymphocytic cells are separated from the pleural effusion of a patient with tuberculosis. More specifically, 100 ml of pleural effusion is collected from the patient by the thoracentesis method, then centrifuged at 1500 r.p.m. for 5 minutes, washed twice with MEM containing 10 units/ml of heparin and centrifuged by the Ficoll-Paque density gradient method to isolate $3 \times 10^8$ lymphocytes from pleural effusion. T cells from pleural effusion are obtained in the same manner as in (1) above. The cells ($1 \times 10^6$/ml) are stimulated with 25 $\mu$g/ml of PPD for 48 hours. The cells thus obtained are referred to as "PPD-stimulated PE-T".

EXAMPLE 3

Fusion of parental cells and human T cells, selection and cloning of the fused cells Parental cells CEM-AGR ® are maintained in a state of brisk growth by replacing the medium (RPMI 1640+10% FCS+100 $\mu$M 8-AG) daily for three days preceding fusion.

CEM-AG ® ($1 \times 10^7$ cells) and each type of the human T cells ($2 \times 10^7$) obtained in Example 2 are used for fusion. The cells are washed three times with FCS-free MEM medium maintained at 37° C., then thoroughly mixed together in a 50-ml conical tube and centrifuged at 1000 r.p.m. for 10 minutes. The pellets of cells separated from the supernatant are lightly shaken, and 0.3 ml of 45% PEG-6000 (Koch-Light Co., England) heated to 37° C. is applied to the pellets. The pellets are then thoroughly shaken for 30 seconds and thereafter allowed to stand at 37° C. for 6 minutes in an incubator containing 5% carbon dioxide and 95% air. FCS-free MEM (heated to 37° C.) is placed into the incubator in a combined amount of 12 ml at a rate of 2 ml/min. A 25 ml quantity of MEM is further added to the mixture quickly, the resulting mixture is centrifuged at 800 r.p.m. for 10 minutes and the supernatant is removed. RPMI 1640 medium containing 20% of FCS and heated to 37° C. is gently added to adjust the concentration of CEM-AG ® to $2 \times 10^5$ cells/ml. A 1 ml quantity of the mixture is placed into each of 50 wells, 2 cm in diameter, of a microculture plate (Linbro Scientific, U.S.A.). In 24 hours, one half of the supernatant is discarded, and 1 ml of HAT medium (RPMI 1640+20% FCS medium, containing $1 \times 10^{-4}$ M of hypoxanthine (Sigma Chemical Co., U.S.A.), $4 \times 10^{-7}$ M of aminopterin (Sigma Chemical Co., U.S.A.) and $1.6 \times 10^{-5}$ M of thymidine (Sigma Chemical Co., U.S.A.) is placed into the well. The same procedure is repeated every two days to culture the cells in an incubator in the presence of 5% of carbon dioxide gas at 37° C. for 2 to 4 weeks. The grown cell lines are then transferred to HT medium not containing aminopterin (A) (corresponding to HAT medium free from A), incubated for another week, thereafter transferred to a HAT-free medium of RPMI 1640+10% FCS (conventional medium) and cloned by the usual method. More specifically, the culture is diluted to 1 hybrid cell/ml in a conventional media and placed into the wells of a microplate (Falcon, U.S.A.) in an amount of 0.2 ml/well. One half of the supernatant is discarded from each well every 2 to 3 days, and a fresh conventional culture medium heated to 37° C. is poured into the well for further incubation, giving rise to monoclones of the hybrid cell lines. The typical of the clones thus obtained, i.e. human T hybrid cell lines, have the characteristics shown in the foregoing Table 2.

EXAMPLE 4

Preparation of culture supernatant from human T hybrid cells (1) Supernatant obtained without stimulation Cells of the hybrid clone obtained in Example 3, namely No. 24-A, are adjusted to a concentration of $1 \times 10^5$ cells/ml as contained in RPMI 1640+10% FCS medium, then placed into the wells, 2 cm in diameter, of a culture plate (Linbro Scientific, U.S.A.) and cultured in an incubator in the presence of 5% carbon dioxide at 37° C. for 2 days. The culture is centrifuged at 3000 r.p.m. for 10 minutes, and the supernatant is collected, filtered with a 0.45 µ millipore filter for sterilization and checked for lymphokine activity.

(2) Con A-stimulated supernatant

A supernatant is prepared in the same manner as the above procedure (1) except that 1 µg/ml of Con A is added to the same medium as used in (1) above. The supernatant is examined for lymphokine activity.

(3) PHA-stimulated supernatant

The concentration of the hybrid clone No. 38-B cells obtained in Example 3 is adjusted to $1 \times 10^5$ cells/ml with use of RPMI 1640+10% FCS 0.1% PHA. A culture supernatant is obtained in the same manner as in (1) above.

(4) Macrophage-stimulated supernatant

Peripheral blood lymphocytes obtained in the same manner as in Example 2-(1) are placed in a Petri dish and the cells which are not adherent to the dish were washed out. The remaining cells which are adherent to the dish are detached by pipetting with HBSS (Hank's balanced salt solution)/0.2% EDTA (a product of Sigma, U.S.A.), and used as human macrophages.

A macrophage-stimulated culture supernatant is obtained in the same manner as in (3) above except that the human macrophages are added to the medium at a concentration of $0.5 \times 10^5$ cells/ml.

EXAMPLE 5

Analysis of lymphokine activity of the culture supernatant from human T hybrid cell lines The culture supernatants prepared in Example 4 are tested for lymphokine activity by the following methods.

(1) Test 1 for TCGF activity of the culture supernatant from clone No. 24-A

Thymocytes are obtained from 5- to 6-week-old BALB/C mice (Shizuoka Agricultural Cooperative Association for Laboratory Animals, Japan), cut into small fragments, washed twice with MEM and suspended in RPMI 1640 medium containing 10% FCS to obtain a cell suspension having a concentration of $1 \times 10^6$ cells/ml. The supernatant from clone No. 24-A obtained in Example 4-(1) or (2) is added to a 0.1 ml portion of the suspension ($1 \times 10^5$ cells), and the mixture is placed into a 0.2-ml flat-bottomed microplate (Falcon). $^3$H-thymidine ($^3$H-TdR) 0.5 µCi/well is added to the mixture during the last 6 hours, and the thymocytes are incubated in the presence of 2 µg/ml Con A for stimulation. On day 3, the culture is checked for $^3$H-TdR uptake. The culture supernatant from CEM-AG ®, i.e. the parental cell line, is similarly tested. The results are shown in FIG. 5, in which the $^3$H-TdR uptake count (C.P.M. $\times 10^{-3}$) is plotted as the ordinate. Indicated at A is the result achieved without using any culture supernatant, at B the result for the supernatant of Example 4-(1) and the result for a supernatant from CEM-AG ® obtained similarly (the blank bar representing the former, the hatched bar the latter, the same as hereinafter), at C the result for the supernatant of Example 4-(2) and the result for a supernatant similarly obtained from CEM-AG ®, and at D the result obtained with use of 1 µg/ml of Con A only in place of the culture supernatant. The results (A) to (D) are indicated all in terms of mean values ±S.D. obtained by repeating the same test three times. FIG. 5 shows that the culture supernatants from clone No. 24-A (unhatched B and C) induce significant proliferation of mouse thymocytes stimulated with Con A and that this activity is especially high in the case of C achieved with the supernatant prepared by stimulating clone No. 24-A with Con A. It is seen that in the case of CEM-AG ®, neither the supernatant prepared without stimulation or the supernatant prepared by stimulation with Con A produces any T cell growth factor.

(2) Test 2 for TCGF activity of the culture supernatant from clone No. 24-A

A 50-ml portion of the supernatant obtained in Example 4-(1) is concentrated and then passed through a Sephadex G-100 column (Pharmacia, Sweden) to obtain a fraction with a molecular weight of about 13000 to about 20000, which is concentrated to 5 ml on Amicon YM-5 membranes (Amicon Corporation, Lexington, Mass.) to prepare a semi-purified supernatant. Similarly a semi-purified supernatant is prepared from the parental cell line CEM-AG ®.

A TCGF-dependent human cytotoxic T cell line is prepared by MLC (mixed lymphocyte culture) reaction between normal human peripheral blood T cells and mitomycin-treated CESS (human B cells transformed with EB-virus and provided by Dr. Peter Ralph of Sloan-Kettering Institute for Cancer Research, New York U.S.A.) and incubating the resulting culture for 16 weeks in TCGF (crude TCGF obtained by culturing $1 \times 10^6$ human tonsillar lymphocytes in the presence of 0.1% of PHA for 2 days and separating the supernatant for use).

The cytotoxic cell line ($3 \times 10^3$) is cultured in the presence of the semi-purified supernatant for 24 hours (in $CO_2$ incubator with use of RPMI 1640+10% FCS medium at 37° C.), and 0.5 $\mu$Ci $^3$H-TdR is pulsed for 5 to 8 hours. The semi-purified supernatant is serially diluted to count the $^3$H-TdR uptake to determine the TCGF activity. The results are shown in FIG. 6, in which the dilution of the supernatant is plotted as the abscissa, 1 being the initial concentration of the supernatant to be diluted and 0 being a control wherein no supernatant is used. The hatched value represents the semi-purified supernatant prepared first, and the unhatched value the semi-purified supernatant from CEM-AG ®. The $^3$H-TdR uptake count (C.P.M. $\times 10^{-3}$) is plotted as the ordinate. All the results shown are mean values $\pm$S.D. obtained by triplicate cultures.

FIG. 6 shows that the semi-purified fraction prepared from the culture supernatant from clone No. 24-A of the invention and having a molecular weight of 13,000 to 20,000 maintains proliferation of the TCGF-dependent human cytotoxic T cell line and that the activity is dependent on the concentration of the soluble factor. It is also seen that the fraction obtained from the parental cell line CEM-AG ® and approximate by equal to the above fraction in molecular weight exhibits no growth activity at any concentration.

(3) Test for TCGF activity of the culture supernatant from clone No. 38-B

The culture supernatants obtained in Example 4-(3) and (4) are tested for TCGF activity in the same manner as in (2) above with use of an assay system employing the TCGF-dependent cytotoxic T cell line. The results are listed below in Table 3, in which the groups A to H mean the following.

A: Control group with no supplement.
B: Group supplemented with the supernatant obtained in Example 4-(4).
C: Group supplemented with the culture supernatant from the parent cell CEM-AG ® obtained in the same manner as in Example 4-(4).
D: Group supplemented with the supernatant obtained in Example 4-(3).
E: Group supplemented with the culture supernatant from the parent cell CEM-AG ® obtained in the same manner as in Example 4-(3).
F: Group supplemented with the human macrophages having a density of $0.5 \times 10^5$ cells/ml and PHA (0.1%)
G: Group supplemented with PHA (0.1%).
H: Group supplemented with a crude TCGF (0.5 unit) obtained by cultivating human tonsil lymphocytes ($1 \times 10^6$ cells/ml) in the presence of 0.1% PHA for two days. (The TCGF activity from $1 \times 10^6$ PHA-stimulated cells is defined as 1 unit of TCGF.)

TABLE 3

| Group | $^3$H-TdR uptake (cpm) |
|-------|------------------------|
| A | 1936 ± 838 |
| B | 5131 ± 1684 |
| C | 2291 ± 865 |
| D | 2170 ± 628 |
| E | 1844 ± 698 |
| F | 1995 ± 1098 |
| G | 711 ± 74 |
| H | 4214 ± 333 |

Table 3 shows TCGF activity of the culture supernatant obtained from the human macrophage-stimulated clone No. 38-B according to the present invention. The supernatant from the parent cell line CEM-AG ® does not show TCGF activity.

We claim:

1. A hypoxanthine-guanine-phosphoribosyl-transferase (HGPRT) deficient human T leukemic cell line which has the identifying characteristics of ATCC number CRL-8081.

2. A human T hybrid cell line which is formed by fusing the cell line of HGPRT deficient human T leukemic cell having the identifying characteristics of ATCC number CRL-8081 with normal human T cells.

3. A cell line as defined in claim 2 wherein the hybrid cell line is capable of producing a lymphokine.

4. A method of producing a lymphokine comprising, culturing a hypoxanthine-guanine-phosphoribosyl-transferase (HGPRT) deficient human T leukemic cell line having the identifying characteristics of ATCC number CR2-8081 under conditions sufficient to form lymphokine.

5. A cell line as defined in claim 2 wherein the hybrid cell line is capable of producing a helper factor.

6. A cell line as defined in claim 2 wherein the hybrid cell line is capable of producing T cell growth factor.

7. A cell line as defined in claim 2 wherein the hybrid cell line has the identifying characteristics of ATCC number HB8082.

8. A method of producing a HGPRT deficient human T leukemia cell line having the identifying characteristics of ATCC number CRL-8081 comprising culturing human T leukemia cell line CCRF-CEM in a medium containing 8-azaguanine and recovering said HGPRT deficient human T leukemia cell line.

9. A method of producing a human T hybrid cell line comprising fusing HGPRT deficient human leukemic T cells having the identifying characteristics of ATCC number CRL-8081 with normal human T cells with use of a fusion promoter.

10. A method of claim 9 further comprising selectively proliferating the hybrid cells resulting from the fusion of said HGPRT deficient human T leukemic cells with normal human T cells in a selective medium.

11. A method of claim 10 wherein the selective medium contains hypoxanthine, aminopterin and thymidine.

12. A method of claim 10 further comprising cloning the hybrid cells to obtain a hybrid cell line having the ability to produce a lymphokine.

* * * * *

UNITED STATES PATENT AND TRADEMARK OFFICE
CERTIFICATE OF CORRECTION

PATENT NO. : 4,544,632
DATED : October 1, 1985
INVENTOR(S) : YAMAMURA et al

It is certified that error appears in the above-identified patent and that said Letters Patent are hereby corrected as shown below:

Column 14, line 35, after "culturing" insert --a human T hybrid cell line which is formed by fusing--.

Column 14, line 38, please change "CR 2-8081" to --CRL-8081 with normal human T cells--.

Signed and Sealed this

Thirteenth Day of September, 1988

Attest:

DONALD J. QUIGG

*Attesting Officer*          *Commissioner of Patents and Trademarks*